US00PP29882P2

(12) United States Plant Patent
Zaiger et al.

(10) Patent No.: US PP29,882 P2
(45) Date of Patent: Nov. 27, 2018

(54) INTERSPECIFIC TREE NAMED 'SHERRI'S FLAVOR'

(50) Latin Name: ***Interspecific Prunus* species**
Varietal Denomination: Sherri's Flavor

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 15/732,461

(22) Filed: Nov. 16, 2017

(51) Int. Cl.
*A01H 5/08* (2018.01)

(52) U.S. Cl.
USPC ..... Plt./180

(58) Field of Classification Search
USPC ..... Plt./180
See application file for complete search history.

*Primary Examiner* — Annette H Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size, yellow flesh fruit.
3. Fruit with an attractive, dark purple skin color.
4. Fruit with very good flavor and eating quality.
5. Fruit with good storage and shipping quality.

1 Drawing Sheet

Botanical designation: Interspecific *Prunus* species.
Variety denomination: 'Sherri's Flavor'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior varieties

Among the existing varieties of interspecific trees, which are known to us, and mentioned herein, 'Dapple Jack' Interspecific (U.S. Plant Pat. No. 18,178), 'Flavor Queen' Interspecific (U.S. Plant Pat. No. 7,420) and the proprietary non-patented interspecific seedlings '63EG291', '45GH111' and '7HC244'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. as an open pollinated seedling selection from our proprietary non-patented seedling '63EG291'. The seed parent (63EG291) originated as an open pollinated seedling selection from the proprietary non-patented interspecific seedling '45GH111', which originated from the cross of the proprietary non-patented interspecific seedling '7HC244' and 'Flavor Queen' Interspecific (U.S. Plant Pat. No. 7,420). A large number of these open pollinated seedlings were planted and maintained on their own root system and under close and careful observation we recognized the desirable tree and fruit characteristics of the present variety and selected it in 2000 for additional asexual propagation and commercialization.

ASEXUAL REPRODUCTION OF THE VARIETY

In 2000 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of large size, freestone fruit with an attractive dark purple skin color. The fruit is further characterized by its firm, yellow flesh, very good flavor and eating quality with good handling and shipping ability. In comparison to its proprietary non-patented interspecific seed parent '63EG291' the fruit of the new variety is approximately 42 days earlier in maturity. In comparison to the commercial variety 'Dapple Jack' Interspecific (U.S. Plant Pat. No. 18,178) the fruit of the new variety has dark purple skin compared to speckled red, is larger in size and is approximately 8 days earlier in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 17 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 17 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, adequate fruit set 15 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 800 hours at or below 45° F.

Trunk:

*Size*.—Large. Average circumference 51.1 cm at 27.9 cm above ground on a 17 year old tree.

*Stocky*.—Medium stocky.

*Texture*.—Medium shaggy, roughness increases with age.

*Color*.—Varies from 2.5Y 2/2 to 5Y 4/2.

Branches:

*Size*.—Medium. Average circumference 15.5 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 14 in a 25.8 square cm area. Average length 5.5 mm. Average width 2.3 mm. Color varies from 7.5YR 5/10 to 7.5YR 4/8.

*Color*.—New growth varies from 2.5GY 6/6 to 7.5YR 3/6. Mature growth varies from 5YR 3/2 to 7.5YR 2/4, varies with age of growth.

Leaves:

*Size*.—Medium to large. Average length 106.7 mm. Average width 47.5 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small to medium. Average length 12.6 mm. Average width 1.8 mm. Longitudinally grooved. Surface — glabrous. Color varies from 2.5GY 6/6 to 7.5R 4/8.

*Glands*.—Type — globose. Size — small to medium. Average length 0.9 mm. Average diameter 0.5 mm. Number varies from 2 to 5, average number 4. Located primarily on the base of leaf blade and upper portion of the petiole. Color varies from 7.5R 4/8 to 10Y 7/6.

*Stipules*.—Average number 2. Average length 10.4 mm. Edges — pectinate. Color 5GY 6/10.

*Color*.—Upper surface 5GY 3/6. Lower surface varies from 5GY 5/4 to 5GY 4/4. Midvein color varies from 2.5GY 8/4 to 5GY 8/4.

Flower buds:

*Size*.—Medium to large. Average length 10.6 mm. Average diameter 5.5 mm.

*Hardiness*.—Hardy with respect to California winters.

*Density*.—Very dense.

*Form*.—Conical, becoming elongated just before opening.

*Pedicel*.—Average length 10.7 mm. Average width 0.3 mm. Surface — glabrous. Color varies from 2.5GY 7/8 to 5GY 7/8.

*Color*.—N 9.5/(white).

*Number of buds per spur*.—Average number 5, varies from 4 to 8.

Flowers:

*Blooming period*.—Date of First Bloom Feb. 25, 2017. Date of Petal Fall Mar. 7, 2017, varies slightly with climatic conditions.

*Size*.—Medium to large. Average height 12.4 mm. Average diameter 22.6 mm.

*Petals*.—Normally 5, alternately arranged to sepals. Size — medium to large. Average length 13.1 mm. Average width 8.2 mm. Form — elliptical. Arrangement — free. Petal apex — rounded. Petal base — truncate. Margin — sinuate. Color N 9.5/(white). Both upper and lower surfaces glabrous.

*Sepals*.—Normally 5, alternately arranged to petals. Size — small. Average length 3.5 mm. Average width 2.6 mm. Shape — triangular. Apex — triangular. Margin — serrulate. Both upper and lower surfaces glabrous. Color — upper surface varies from 2.5GY 7/6 to 2.5GY 6/6. Lower surface varies from 2.5GY 6/8 to 2.5GY 6/6.

*Stamens*.—Average number per flower 28. On average, the stamens are above the height of the petals. Average filament length 9.6 mm. Filament color N 9.5/(white). Anther color varies from 10YR 6/10 to 2.5Y 8/10.

*Pollen*.—Self sterile, pollinator required. Color varies from 2.5Y 8/12 to 5Y 7/10.

*Pistil*.—Number — normally 1. Average length 12.0 mm. Position of stigma even with anthers. Surface — glabrous. Color varies from 10Y 8/4 to 10Y 8/6.

*Fragrance*.—Heavy aroma.

*Color*.—N 9.5/(white).

*Pedicel*.—Average length 12.0 mm. Average width 0.4 mm. Color varies from 5GY 7/8 to 5GY 6/8.

*Number flowers per flower bud*.—Average number 2, varies from 1 to 4.

Fruit:

*Maturity when described*.—Firm ripe and ready for consumption.

*Date of first picking*.—Jun. 30, 2017.

*Date of last picking*.—Jul. 10, 2017, varies slightly with climatic conditions.

*Size*.—Large. Average diameter axially 65.6 mm. Average transversely in suture plane 66.2 mm. Average weight 161.9 grams, varies slightly with fertility of the soil, amount of thinning and climatic conditions.

*Form*.—Globose.

*Suture*.—Slightly lipped.

*Ventral surface*.—Slightly lipped.

*Apex*.—Very slightly. retuse.

*Base*.—Nearly flat to slightly retuse.

*Stem cavity*.—Rounded to slightly elongated in suture plane. Average depth 2.8 mm. Average diameter 7.2 mm.

Stem:

*Size*.—Medium. Average length 13.9 mm. Average diameter 1.6 mm.

*Color*.—Varies from 10YR 4/6 to 10Y 6/8.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Slight aroma.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 17.5°, varies slightly with amount of fruit per tree and climatic conditions.

*Color*.—Varies from 2.5Y 8.5/8 to 2.5Y 8/8.

*Pit cavity*.—Average length 27.0 mm. Average width 20.0 mm. Average depth 7.0 mm. Color varies from 10YR 7/8 to 2.5Y 8/8.

Skin:

*Thickness*.—Medium.

*Surface*.—Smooth to slightly waffled.

*Bloom*.—Moderate amount, complete coverage.

*Tendency to crack*.—Very slight.

*Color*.—Ground color varies from 10YR 9/2 to 10YR 8/4. Overspread with 7.5R 2/2 to 5R 2/2.

*Tenacity*.—Tenacious to the flesh.

*Astringency*.—Undetected.

Stone:

*Type*.—Freestone, weak adherence to flesh.

*Size*.—Medium. Average length 25.3 mm. Average width 18.5 mm. Average thickness 10.2 mm.

*Form*.—Ovoid.

*Base*.—Flat.

*Apex*.—Pointed. Average length 2.5 mm.

*Surface*.—Slightly pitted throughout. One shallow groove on each side of suture extending from base to apex.

*Sides*.—Unequal, one side extending further from suture plane.

*Ridges*.—Small, extending from base toward apex.

*Tendency to split*.—Slight.

*Color*.—Varies from 10YR 7/6 to 10YR 6/8 when dry.

Kernel:

*Size*.—Medium. Average length 16.3 mm. Average width 10.7 mm. Average depth 6.0 mm.

*Form*.—Ovate.

*Viability*.—Viable, complete embryo development.

*Skin color*.—Varies from 2.5Y 8/6 to 5Y 9/6.

Use:

*Dessert*.—Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

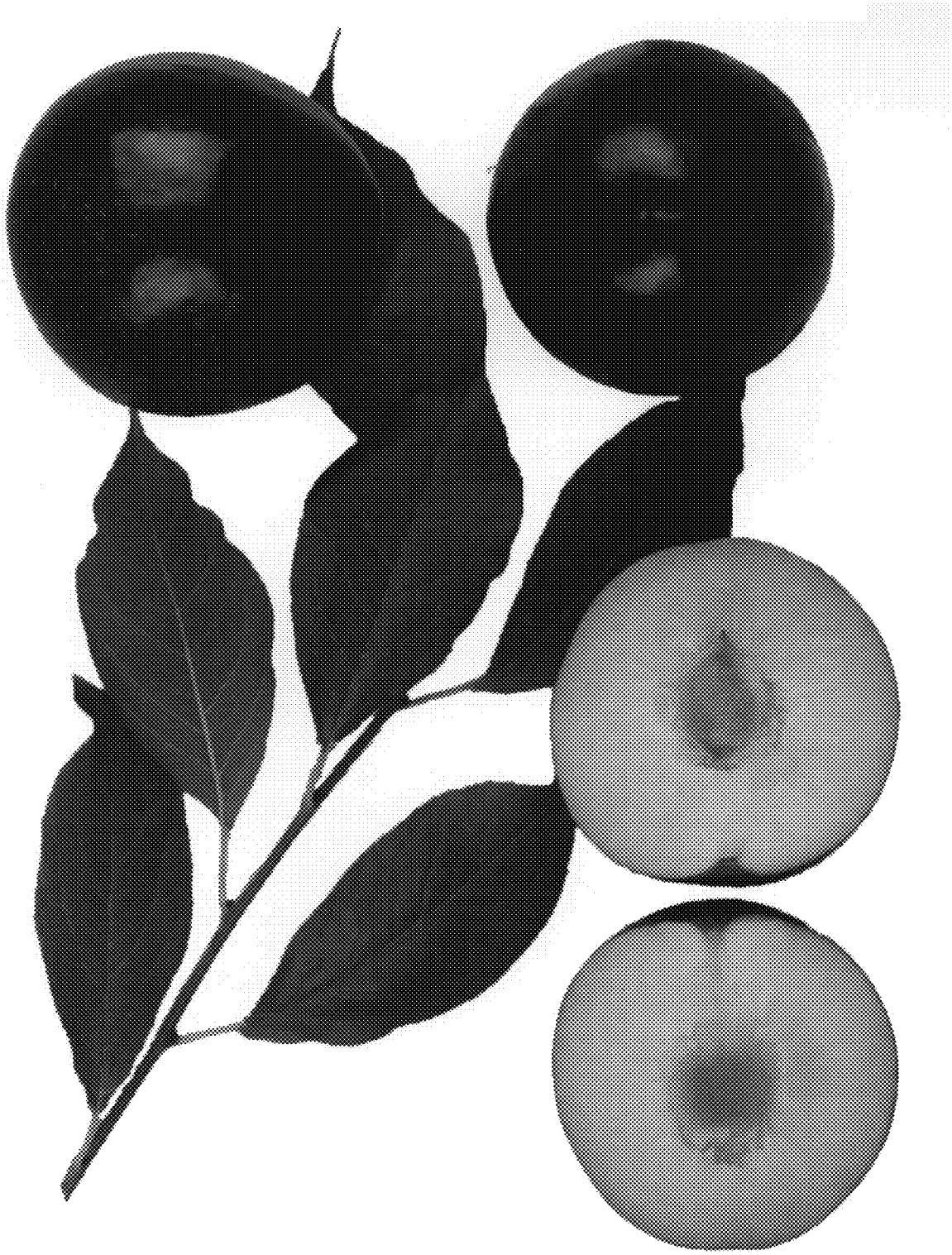

* * * * *